US012352741B2

(12) United States Patent
Silvestre Duarte et al.

(10) Patent No.: US 12,352,741 B2
(45) Date of Patent: Jul. 8, 2025

(54) APPARATUS AND METHOD FOR MEASURING DEGRADATION KINETICS OF A BIOMATERIAL IN AQUEOUS SOLUTION BELOW THE NORMAL FREEZING TEMPERATURE

(71) Applicant: SMARTFREEZ, LDA, Porto Salvo (PT)

(72) Inventors: Andreia Filipa Silvestre Duarte, Sacavém (PT); Pedro Gil Sena Rego, Lisbon (PT); Rui De Brito Estrela, Lisbon (PT)

(73) Assignee: SMARTFREEZ, LDA, Porto Salvo (PT)

( * ) Notice: Subject to any disclaimer, the term of this patent is extended or adjusted under 35 U.S.C. 154(b) by 1094 days.

(21) Appl. No.: 16/980,115

(22) PCT Filed: Mar. 12, 2019

(86) PCT No.: PCT/IB2019/051995
§ 371 (c)(1),
(2) Date: Sep. 11, 2020

(87) PCT Pub. No.: WO2019/175767
PCT Pub. Date: Sep. 19, 2019

(65) Prior Publication Data
US 2021/0018485 A1 Jan. 21, 2021

(30) Foreign Application Priority Data
Mar. 12, 2018 (PT) .......................... 110619

(51) Int. Cl.
*G01N 33/48* (2006.01)
*G01N 21/25* (2006.01)
(Continued)

(52) U.S. Cl.
CPC ............. *G01N 33/48* (2013.01); *G01N 21/25* (2013.01); *G01N 31/22* (2013.01); *G01N 33/15* (2013.01)

(58) Field of Classification Search
CPC ........ G01N 33/48; G01N 21/25; G01N 31/22; G01N 33/15
See application file for complete search history.

(56) References Cited

U.S. PATENT DOCUMENTS

| 2012/0040450 A1 | 2/2012 | Clarke et al. | |
| 2012/0293338 A1* | 11/2012 | Chaffey | G01K 1/024 340/870.02 |

(Continued)

FOREIGN PATENT DOCUMENTS

WO  WO 2005/103686 A1  11/2005

OTHER PUBLICATIONS

Brummitt, R.K. et al.: "Nonnative Aggregation of an IgGI Antibody in Acidic Conditions, Part 2: Nucleation and Growth Kinetics with Competing Growth Mechanisms", Journal of Pharmaceutical Sciences, vol. 100, No. 6, 2011, pp. 2104-2119.

(Continued)

*Primary Examiner* — Samuel P Siefke
(74) *Attorney, Agent, or Firm* — Leason Ellis LLP (57) ABSTRACT

This present disclosure describes an apparatus and a method for measuring degradation kinetics of a biomaterial in aqueous solution below the normal freezing temperature. Further includes new systems comprising high-pressure containers with nucleating-locks, a temperature-control holder for the high-pressure containers, a holder for the nucleating-locks and an insulated low-temperature gradient chamber. A method is described comprising several steps such as filling of the high-pressure container with the biomaterial solution to be slightly below freezing temperature, closing of the (Continued)

container with a nucleating-lock, which is below freezing temperature, allowing the container to reach the reaction temperature, removing the container at selected time and bringing it to above freezing temperature and opening the container to recover the biomaterial solution.

15 Claims, 8 Drawing Sheets

(51) Int. Cl.
*G01N 31/22* (2006.01)
*G01N 33/15* (2006.01)

(56) References Cited

U.S. PATENT DOCUMENTS

| | | | |
|---|---|---|---|
| 2016/0154004 A1 | 6/2016 | Roberts et al. | |
| 2018/0024032 A1* | 1/2018 | Hollabaugh | F16H 57/08 475/331 |
| 2018/0064100 A1* | 3/2018 | Morris | A01N 1/0268 |

OTHER PUBLICATIONS

Rosa, M.; Roberts, C.J.; Rodrigues, M.A., "Connecting high-temperature and low-temperature protein stability and aggregation", PLOS ONE, vol. 12, No. 5, May 4, 2017 (May 4, 2017), p. 1-12.

Powell-Palm Matthew J et al., "*Escherichia coli* viability in an isochoric system at subfreezing temperatures", Cryobiology, vol. 85, Dec. 2018 (Dec. 2018), p. 17-24.

Lyu, Chenang et al., "A comparison of freezing-damage during isochoric and isobaric freezing of the potato", May 18, 2017 (May 18, 2017), p. 1-15, online, Retrieved from the Internet: URL:https://pdfs.semanticscholar.org/bf02/adafef368d91eea2601709f1317e8ff84675.pdf, XP002792664, [retrieved on Jun. 30, 2020].

Ukpai Gideon et al, "Pressure in isochoric systems containing aqueous solutions at subzero Centigrade temperatures", PLOS ONE, vol. 12, No. 8, Aug. 17, 2017 (Aug. 17, 2017), p. 1-16.

Rubinsky Boris et al, "The thermodynamic principles of isochoric cryopreservation", Cryobiology, vol. 50, No. 2, Apr. 2005 (Apr. 2005), p. 121-138.

Rosa M. et al., Measuring and modeling hemoglobin aggregation below the freezing temperature, Journal of Physical Chemistry B, 117(30), pp. 8939-8946, 2013.

* cited by examiner

APPARATUS AND METHOD FOR MEASURING DEGRADATION KINETICS OF A BIOMATERIAL IN AQUEOUS SOLUTION BELOW THE NORMAL FREEZING TEMPERATURE

CROSS-REFERENCE TO RELATED APPLICATIONS

This application is a U.S. National Stage Application under 35 U.S.C. § 371 of International Patent Application No. PCT/IB2019/051995, filed Mar. 12, 2019, which claims priority to Portugal Patent Application No. 110619, filed Mar. 12, 2018, the contents of which are each hereby incorporated by reference in their respective entireties.

TECHNICAL FIELD

This disclosure relates, in general to an apparatus and a method for measuring degradation kinetics of a biomaterial in aqueous solution below the normal freezing temperature.

BACKGROUND

Protein aggregation is a long-standing problem for preservation of proteins in both laboratory settings and for commercial biotechnology products. This is a frequent problem during the manufacture and storage of proteins, and it can be the cause of immunogenicity (small aggregates) or potential problems with administration (large aggregates). Therefore, as part of the drug development process, regulators require stability studies that attest molecules continuous safety and efficacy through its production pathway and shelf-life. Stability of various formulations is generally evaluated by a combination of real-time and accelerated stability studies. However, aggregation during long-term or short-term cold storage is often difficult to predict from typical "accelerated" conditions.

Recently, an expedite method was proposed to accelerate cold denaturation of proteins, by cooling the biomaterials solutions below its freezing temperature, under isochoric conditions in high-pressure containers to prevent the formation of ice (Rosa et al. 2013).

The method described by Rosa et al. (2013) has the potential to improve the common practice used for accelerated studies, which consists essentially in increasing the temperature of the formulations (typically above 50° C.) to obtain degradation rates under reasonable time scales (from hours to weeks). There is a general concern regarding the classical accelerated stability experiments by increasing temperature, that linear Arrhenius extrapolation to the actual cold storage temperature, can grossly overestimate the low-temperature stability of protein solutions (Brummitt et al. 2011; Rosa et al. 2017). Proteins are expected to unfold either by increasing or decreasing temperature from the maximum stability value. For this reason, by enabling to run experiments below freezing temperature without water crystallization, one can perform accelerated stability studies at cold temperatures, thus eliminating the need for extrapolating the results over large temperature ranges, and thereby minimizing the impact of non-Arrhenius behavior.

The isochoric cooling method developed by Rosa et al. (2013) has therefore the potential to clarify protein degradation routes and assist the development of better formulations for enhanced protein stability.

While the fundamental concept of the isochoric method is already established, several limitations must be overcome before the method proposed by Rosa et al. (2013) can find generalized use. Unanticipated issues with the isochoric method have been further identified during the research development and are described subsequently. Rosa et al. (2013) emphasize that the insertion of the ice seeds is essential to ensure that controlled nucleation occurs and that the ice seeds will provide a natural piston when the container is completely full of liquid. As temperature is lowered the low-density ice attempts to grow, but therefore compresses the solution, raising the pressure and suppressing the freezing line, thereby enabling the solution to effectively avoid freezing. Otherwise, the pressure can rise abruptly once uncontrolled nucleation occurs, with adverse effects on protein stability and the reproducibility of the experiment. The authors also use high-pressure containers with a large aspect ratio (length/diameter), which are heavy, hard to close/open, very difficult to clean and sterilize, and therefore time-consuming and poorly reproducible. Moreover, require visual inspection of a long tubular steel container and user experience to ensure that no air is left inside after the addition of the biomaterial solution (otherwise water can expand and freeze) and that the ice seed does not thaw during filling and while the container is being operated above freezing temperature. However, Rosa et al. (2013) did not describe how to ensure that these critical issues are attained, for example how to ensure that the ice seeds stays frozen when mixed with the pharmaceutical formulation above the freezing temperature. Several techniques to control ice nucleation have been proposed, like the introduction of a small ice crystal or heterogeneous nucleators of ice into the sample; by manually generating a cold spot on the outside of the container; by electrofreezing; by mechanical methods (shaking, application of ultrasound); by shock cooling or by pressure shift. Despite many methods have been developed, most are difficult to standardize and to integrate to multiple small-volume containers with reproducibility. Moreover, most methods that have been described to improve ice nucleation use volumes larger than 10 mL and have several disadvantages to be used in the proposed isochoric method. For instance, the addition of external particles to the sample could affect the aggregation kinetics, the use of probes is laborious, all the solution could freeze before the container is closed and the mechanical methods affect the reproducibility.

The isochoric method proposed by Rosa et al is implemented in 8 steps, namely:
(1) filling the container with a fixed volume of water near room temperature;
(2) placing the container at low temperature (such as −20° C. or below) to ensure the crystallization of the water seed;
(3) bringing the container and the biomaterial solution to near freezing temperature;
(4) filling the container with the biomaterial solution, slightly below freezing temperature, so that the ice seed does not melt and also does not grow (freezing the biomaterial solution), also ensuring that air bubbles are not trapped inside;
(5) closing the container;
(6) bringing the container to the reaction temperature;
(7) removing the container at selected time and bringing it to above freezing temperature;
(8) opening the container to recover the biomaterial solution for complementary analytic characterization.

Step 4 is particularly complex and limiting of the overall consistency, especially if many samples must start at the same time. For instance, step 4 requires that significant attention is given to each container; therefore compromising the consistency in the thermal history of 10 or 100 containers that should start at the same time. Moreover, air bubbles are likely to be entrapped by the ice seed that formed in the previous steps, which can break the isochoric conditions of the liquid, allowing the full sample to freeze. In small-volume samples, for instance less than 1 mL, it is easier to ensure that no air is entrapped if the channel is empty when filling the container with the biomaterial solution, i.e. without a frozen portion limiting the access and flow of the biomaterial solution that must be inserted.

Overall, for all the reasons presented, further development is necessary for the isochoric method to be amenable of implementation using automated or semi-automated equipment, which is essential to increase reproducibility, decrease laboriousness and enable high-throughput analysis (many samples with small volume), which is highly desirable for commercial purposes.

SUMMARY

The present disclosure solves the prior art problems by filling the high-pressure container with the biomaterial in aqueous solution and keeping it the biomaterial in aqueous solution at a temperature that is slightly below its freezing temperature at atmospheric pressure such that the biomaterial in aqueous solution does not freeze neither nor the nucleation is induced. Furthermore, when closing the container with the nucleating-lock, the nucleation is induced.

An object of the present disclosure is to provide methods and apparatuses for measuring degradation kinetics of biomaterials in aqueous solutions below the normal freezing temperature without complicated protocols and high reproducibility.

The degradation kinetics of biomaterials in aqueous solutions is defined as the reduction of the concentration of the therapeutically active species per unit of time.

A biomaterial is defined as a protein, an amino acid, a peptide, DNA, RNA, or mixtures thereof. Thus, a biomaterial in an aqueous solution is defined as a protein solution or formulation, an amino acid solution or formulation, a peptide solution or formulation, a DNA solution or formulation, a RNA solution or formulation, or mixtures thereof. A biomaterial or a biomaterial solution can also be defined as a biological material or a biological material solution, respectively.

A normal freezing temperature is defined as the temperature at which the solution freezes at atmospheric pressure.

A reaction temperature is defined as the temperature, in particular the test temperature, at which the experimental runs are hold for the determination of the degradation kinetics. This temperature is pre-determined and depends on the biomaterial in aqueous solution for which one intends to determine the degradation kinetics.

The nucleation temperature is defined as the temperature at which occurs the formation of the first ice crystals in the solution.

The present disclosure provides a method for measuring degradation kinetics of biomaterials in aqueous solutions below the normal freezing temperature comprising the following steps:
  filling the high-pressure container with the biomaterial solution to be slightly below freezing temperature (for example 0.1° C. to 3° C. below), closing the container with a nucleating-lock, which is below freezing temperature (more than 10° C. below), allowing the container to reach the reaction temperature, removing the container at selected time and bring it to above freezing temperature, opening the container to recover the biomaterial solution for complementary analytic characterization.

In an embodiment of the method, the temperature of the high-pressure containers is controlled by means of a temperature-control holder; in particular with means to be positioned at different heights in a low-temperature gradient chamber; more in particular the temperature-control holder has a heater. In another embodiment, the high-pressure container has multiple cavities; in particular the high-pressure container has cavities having two opposing openings. In another embodiment, the nucleating-lock comprises a compressing-lid and a plug with a retainer; in particular the nucleating-lock comprises a compressing-lid and multiple plugs with retainers; more in particular the plug of the nucleating-lock comprises a cavity to hold an ice seed, even more in particular the plug of the nucleating-lock comprises a nucleating agent, such as silver-iodide inside a cavity; the plug of the nucleating-lock comprises a nucleating agent coated by a water permeable material. In an embodiment, the holder cools the nucleating-locks to nucleation temperature. In an embodiment, the insulated low-temperature gradient chamber has a heat exchange mechanism on the bottom surface.

In particular, the present disclosure relates to a method for measuring degradation kinetics of a biomaterial in aqueous solution, comprising the following steps:
  filling a high-pressure container with the biomaterial in aqueous solution and submitting said biomaterial to a temperature below the freezing temperature of the biomaterial at atmospheric pressure;
  closing the high-pressure container with a nucleating-lock, wherein the nucleating-lock is at a temperature below the freezing temperature of the biomaterial at atmospheric pressure;
  allowing the high-pressure container to reach a pre-determined temperature, in particular a pre-determined test temperature, different from the freezing temperature of the biomaterial at atmospheric pressure;
  removing the high-pressure container at a selected time and placing it at a temperature higher than the freezing temperature of the biomaterial at atmospheric pressure; and
  opening the high-pressure container for recovering the biomaterial in aqueous solution for complementary analytic characterization;
  wherein the degradation kinetics of the biomaterial in aqueous solution is measured at a temperature below the freezing temperature of the biomaterial at atmospheric pressure.

In an embodiment, the step of filling the high-pressure container with the biomaterial in aqueous solution and submitting said biomaterial to a temperature below the freezing temperature of the biomaterial at atmospheric pressure is carried out at a temperature of 0.1° C.-3° C. below the freezing temperature of said biomaterial, preferably at a temperature of 0.5° C.-1° C. below the freezing temperature of the biomaterial.

In an embodiment, the step of closing the high-pressure container with the nucleating-lock, wherein said nucleating-lock is at least 10° C. below the freezing temperature of the biomaterial at atmospheric pressure.

In an embodiment, the step of allowing the high-pressure container to reach the pre-determined temperature is carried out by of allowing the high-pressure container to reach −30° C.-0° C.

In an embodiment, the selected time is at least 5 min, at least 10 min, at least 15 min, at least 30 min.

In an embodiment, the biomaterial in aqueous solution is selected from a protein, an amino acid, a peptide, DNA, RNA, or mixtures thereof.

Another important aspect of the disclosure relates to an apparatus or system for measuring degradation kinetics of biomaterials in aqueous solutions below the normal freezing temperature, in particular at atmospheric pressure, comprising an insulated low-temperature gradient chamber, with a temperature-control holder for high-pressure containers, and nucleating-locks. The apparatus or system further comprises a holder to cool the nucleating-locks to the nucleation temperature.

In particular, the present disclosure also relates to an apparatus for measuring degradation kinetics of a biomaterial in aqueous solution, comprising:

a high-pressure container;

an insulated low-temperature gradient chamber comprising a temperature-control holder for the high-pressure container, and a nucleating-lock for inducing the nucleation of water crystals while closing the high-pressure container;

such that the degradation kinetics of the biomaterial in aqueous solution is measured at a temperature below the freezing temperature the biomaterial at atmospheric pressure.

In an embodiment, the apparatus may further comprise a holder for cooling the nucleating-locks to a nucleation temperature.

In an embodiment, the apparatus may further comprise a high-pressure container, wherein the temperature of the high-pressure container is controlled by means of a temperature-control holder.

In an embodiment, the temperature-control holder may comprise means for being positioned at different heights in the insulated low-temperature gradient chamber.

In an embodiment, the temperature-control holder may comprise a heater.

In an embodiment, the high-pressure container may have multiple cavities.

In an embodiment, the high-pressure container may have multiple cavities, wherein each cavity has two opposing openings.

In an embodiment, the nucleating-lock may comprise a compressing-lid and a plug with a retainer.

In an embodiment, the nucleating-lock may comprise a compressing-lid and multiple plugs with retainers.

In an embodiment, the plug of the nucleating-lock may comprise a cavity for holding an ice seed.

In an embodiment, the plug of the nucleating-lock may comprise a nucleating agent, preferably wherein the nucleating agent is silver-iodide, more preferably wherein the nucleating agent is silver-iodide inside a cavity, in particular a cavity of the plug.

In an embodiment, the plug of the nucleating-lock may comprise a nucleating agent coated by a water permeable material.

In an embodiment, the apparatus may further comprise an insulated low-temperature gradient chamber with a heat exchange mechanism on the bottom surface.

BRIEF DESCRIPTION OF THE DRAWINGS

These and other objects, features and advantages of the disclosure will be evident from the following detailed description when read in conjunction with the accompanying drawings.

FIG. 1a is an elevated view of a high-pressure container 100 with a nucleating-lock 102 in accordance with present disclosure.

FIG. 1b is a cross-sectional view of the high-pressure container 100 with a nucleating-lock 102 of FIG. 1a.

DETAILED DESCRIPTION

As presented above, the current implementation of the isochoric method is not compliant with typical industrial-commercial requirements, compromising its generalized use as for protein formulation development or stability evaluation, which typically requires many samples with different compositions, namely different concentrations, excipients, pH values, etc., small volumes, with high reproducibility and with minimal intervention from operators. These requirements, are approached by the method and apparatus disclosed herein, which executes a method for measuring protein degradation kinetics in aqueous solutions below the normal freezing temperature in less steps than the prior art, namely:

filling the container with the biomaterial solution to be slightly below freezing temperature (for example 0.1° C. to 3° C. below), closing the container with a nucleating-lock, which is below freezing temperature (more than 10° C. below), allowing the container to reach the reaction temperature, removing the container at selected time and bringing it to above freezing temperature and opening the container to recover the biomaterial solution for complementary analytic characterization.

Herein, it is disclosed a new apparatus that enable high reproducibility, easy to operation, cleaning and sterilization. These apparatuses comprise high-pressure containers with nucleating-locks, a temperature-control holder for the high-pressure containers, a holder for the nucleating-locks and an insulated low-temperature gradient chamber.

Figures 1A, 1B:
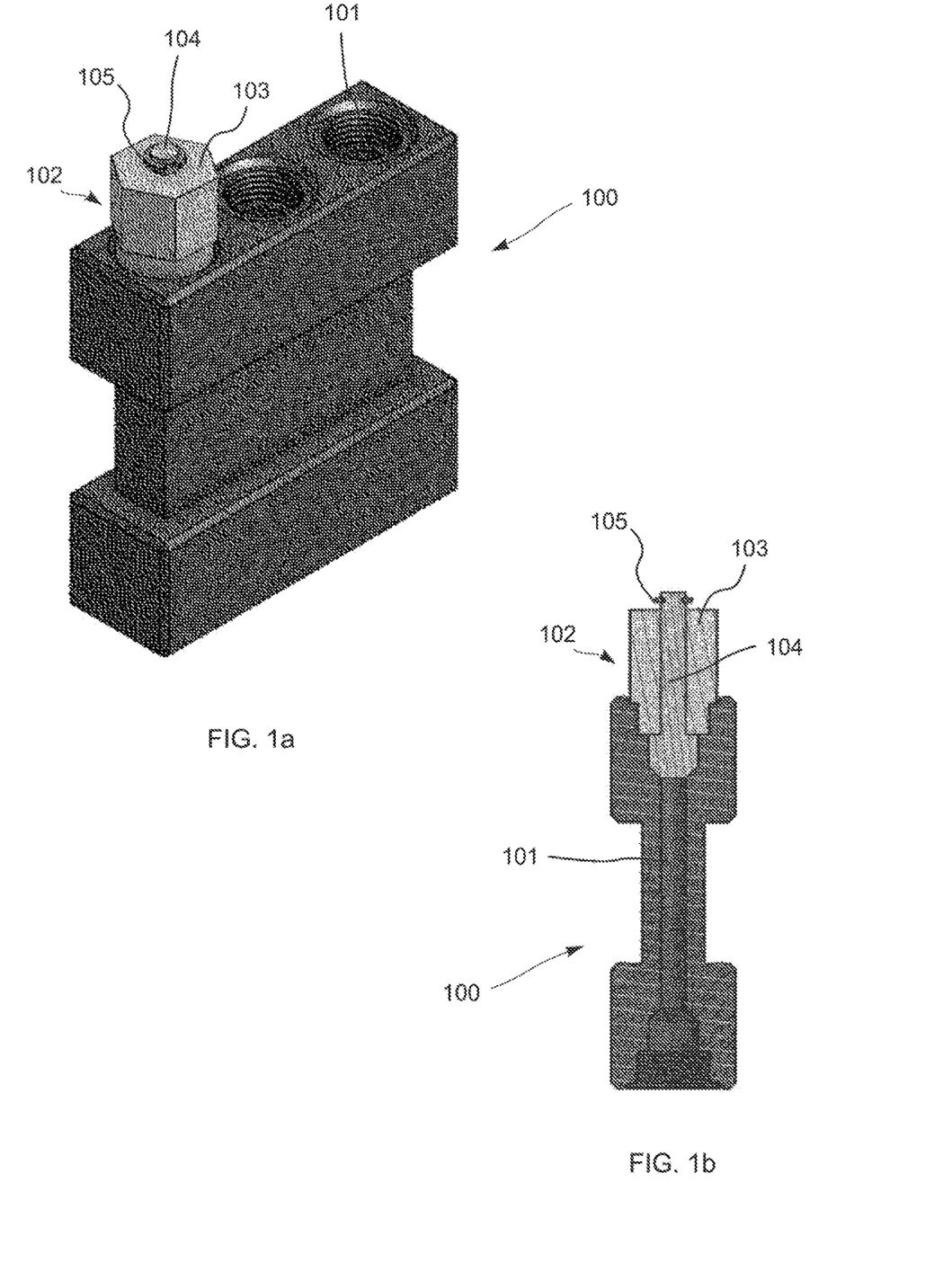

One exemplary embodiment of the present disclosure is depicted in FIG. 1a and FIG. 1b, a high-pressure container 100 with 3 cavities 101 for holding the testing biomaterial solution, preferably biomaterial in aqueous solution. The cavities 101 have at least one opening and are closed with a nucleating-lock 102 per cavity. The cavities 101 for holding the biomaterial solution could have an opening in both sides, two opposing openings, to facilitate the cleaning.

Figure 2:
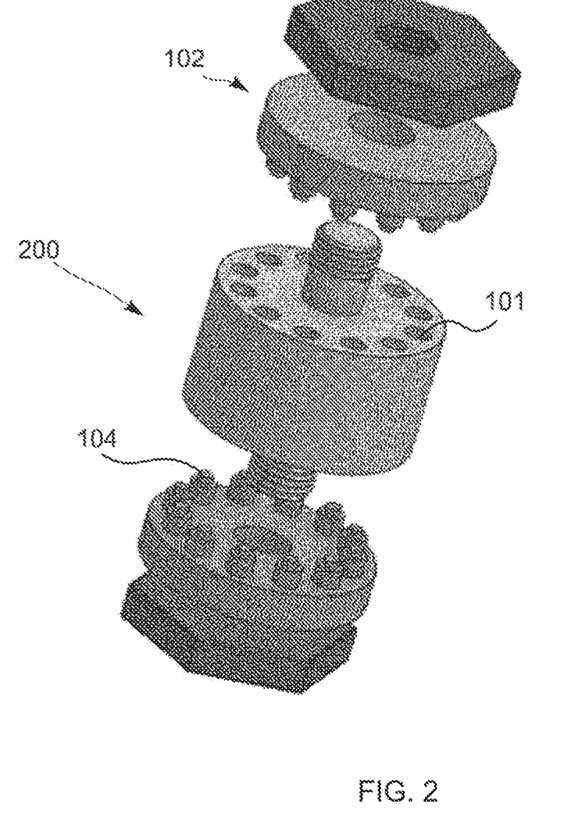
FIG. 2 is a perspective exploded view of another high-pressure container 200 in accordance with present disclosure.

In an alternative embodiment (FIG. 2) the high-pressure container 200 could have more or less cavities 101 for holding the testing biomaterial solution, preferably biomaterial in aqueous solution, which can also be radially disposed.

Figure 3:
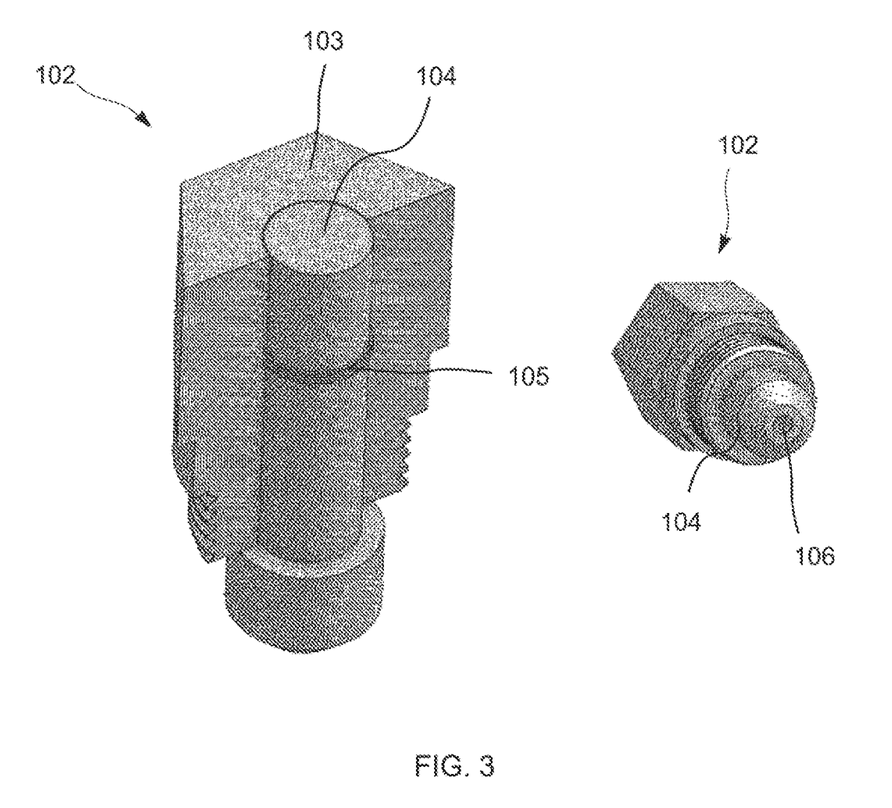
FIG. 3 is a partial cross-sectional and bottom view and of a nucleating-lock 102 in accordance with present disclosure.

As shown in FIG. 3, the nucleating-lock 102 has a compressing-lid 103 and a plug 104 with a retainer 105.

The retainer 105 prevents the detachment of the plug 104 from the plug-compressing-lid assembly and also insulates the plug from the compressing-lid to hold its temperature below the freezing temperature when the operator touches the compressing-lid to close the high-pressure container.

The compressing-lid 103 has the function of compressing the plug 104 into the cavity's, closing the container up to 300 MPa. The compression may be achieved by means of a screw, hydraulic piston, or other means to drive force.

The nucleating-lock 102 has two simultaneous functions, which is a new approach in the field of application, i.e. a high-pressure lock that induces the nucleation of water crystals while it closes the container. Said nucleating-lock may be used to attain the method previously described. First, the high-pressure containers are filled with the biomaterial solution to be slightly below freezing temperature and then the containers are closed with the nucleating-lock, which is typically more than 10° C. below freezing temperature. Since the biomaterial solution is at a temperature near the freezing and the nucleating-lock is below freezing temperature, when the tip of the plug of the nucleating-lock contacts the surface of the biomaterial solution the nucleation is induced, and an ice layer is formed acting as a natural piston and ensuring the isochoric conditions. Therefore, the use of this nucleating-lock eliminates the need of inserting an ice seed inside the container, thus avoiding the issues associated. Nucleation is a stochastic phenomenon with higher probability of occurring for decreasing local temperature. For this reason, the plug of the nucleating-lock should be typically below −20° C. to induce nucleation, under minimal handling by the operator to lock the high-pressure container. Associating complementing nucleation strategies may increase the required temperature. For example, in another embodiment (FIG. 3), the tip of the plug of the nucleating-lock may have a small cavity 106 to place or form an ice seed.

In other embodiment, the cavity of the plug may hold an ice nucleating agent such as silver iodide, which can be coated with a porous material, water permeable, to allow water to reach the nucleation agent while minimizing its detachment or leaching.

The high-pressure containers and nucleating-locks can be made of stainless steel AISI 316 to withstand a maximum pressure of about 300 MPa. The design can be optimized to increase and standardize the heat transfer in the cavities, thus increasing the reproducibility of the method. This is achieved for example by minimizing the thickness of lateral walls, without compromising the size of the compressing-lids of the nucleating-lock that are desirable for easy operation. The high-pressure containers and nucleating-locks can be clean with appropriate washing solutions and/or by using ultrasounds, in accordance with the biomaterials solutions used and could be sterilized by autoclave steam sterilization or other methods of sterilization.

Figure 4:
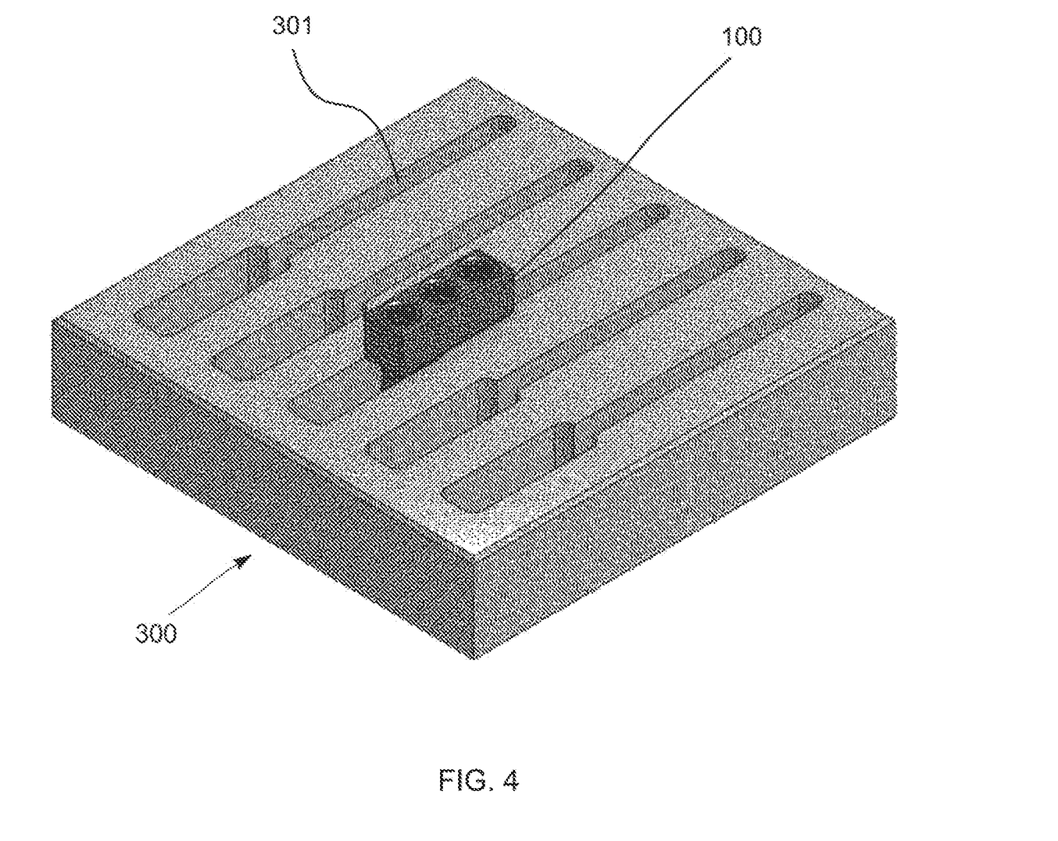
FIG. 4 is an elevated view of a temperature-control holder 300 with a high-pressure container 100 in accordance with present disclosure.

Another embodiment is displayed in FIG. 4, a temperature-control holder 300 with means to be positioned at different heights enabling the high-pressure containers 100 to be at the desired temperature. For example, the temperature-control holder 300 can be lifted or inclined, using an eccentric wheel, levers, screws or hydraulic pistons. The temperature-control holder can have lateral insulation to attenuate heat transfer, for example from the region that is at lower temperature when it is inclined. The temperature-control holder 300 supports several high-pressure containers 100, working as a vise to facilitate the closing of the containers and helping to maintain uniform temperature in all the containers and consequently increasing the reproducibility of the method. The temperature-control holder is made of a metal, typically aluminum and may have fins 301 to accommodate the high-pressure cells and to enhance heat transfer. The temperature-control holder may also have heating means, such as an electric resistance or fluid jacket for improving temperature control dynamics.

Said temperature-control holder 300 may be used to attain the method previously described. In a first step, the high-pressure containers are filled with the biomaterial solution in a chamber with a low-temperature gradient ranging from −20° C. or below (at the bottom surface) and up to near freezing temperature (at the top surface), with the assistance of the temperature-control holder positioned at the height that enables the container to be slightly below freezing temperature. Then the containers are closed with the nucleating-locks, which are inside the low-temperature gradient chamber, at the coldest level, typically at a temperature of −20° or below. Alternatively, the nucleating-locks may be in an auxiliary chamber or compartment at low temperature. Finally, the temperature-control holder is lowered on the bottom surface of the low-temperature gradient chamber to allow all the containers to reach the reaction temperature at the same time.

Figure 5:
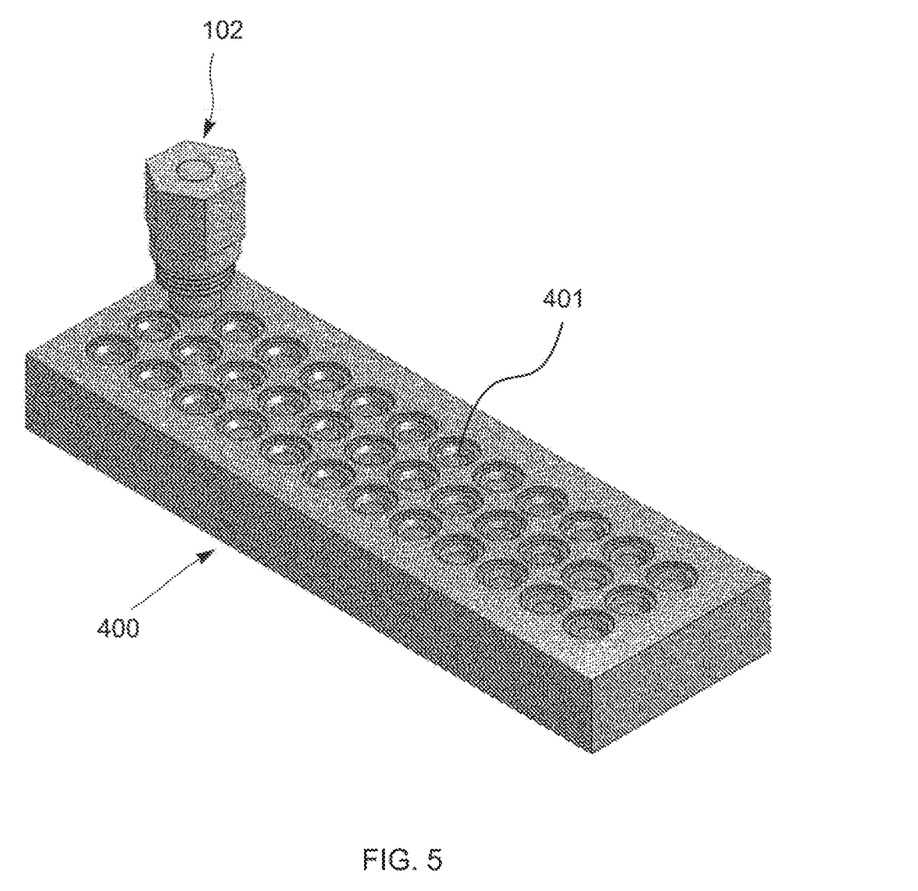
FIG. 5 is an elevated view of a holder for the nucleating-locks 400 in accordance with present disclosure.

In another embodiment (FIG. 5) the apparatus comprises a holder for the nucleating-locks 400. The nucleating-locks 102 are placed in said holder 400, which can have cavities 401 to accommodate the plugs allowing more efficient heat transfer and access to the operator. Said holder with the nucleating-locks is typically at a temperature of −20° C. or below to induce the nucleation when the nucleating-locks close the high-pressure containers. When complementing nucleation strategies are implemented, as described above, the holder and nucleating-locks may be set for higher nucleation temperatures. Said holder for the nucleating-locks is in contact with a heat exchange mechanism on the bottom surface or alternatively inside a low temperature chamber or compartment.

Another embodiment comprises an insulated low-temperature gradient chamber with a heat exchange mechanism on the bottom surface. The insulated low-temperature gradient chamber may further comprise a control utility for controlling the operational steps of the method. The control utility may comprise a visual display and microprocessor or computer or external desktop or laptop computer and may also comprise a user interface allowing a user to control the operational steps of the method.

Figure 6:
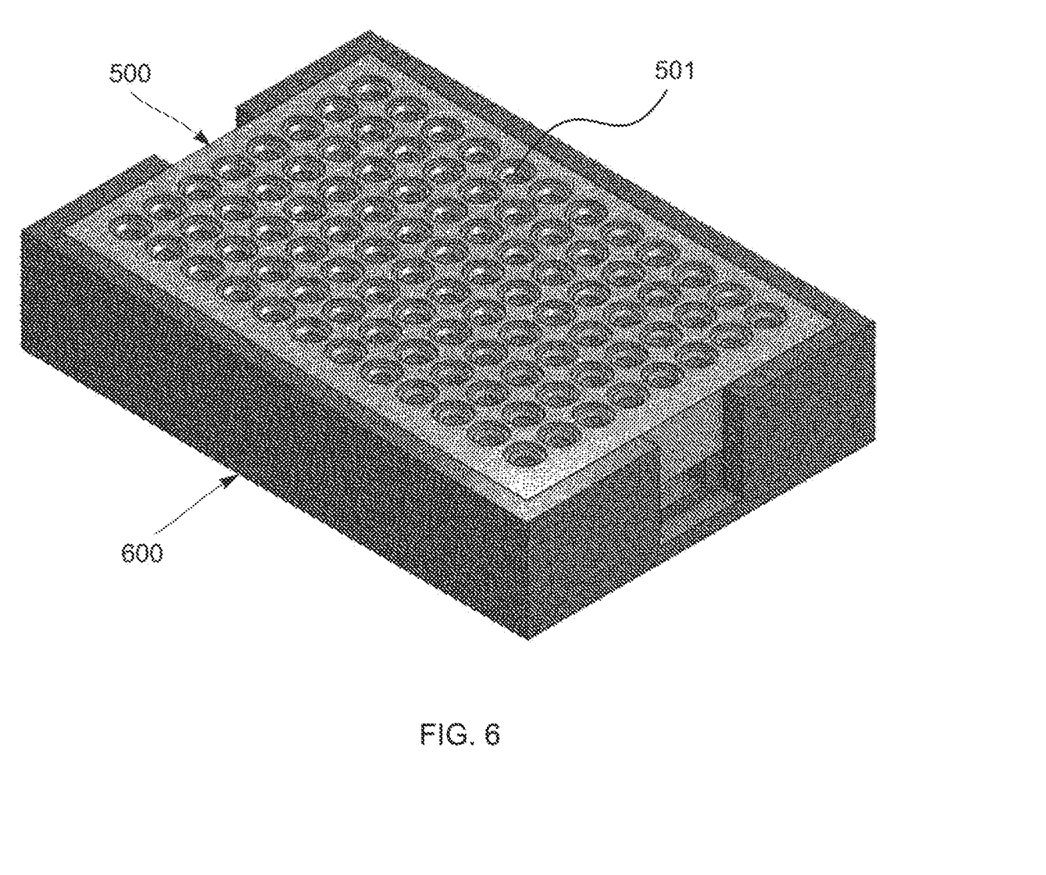
FIG. 6 is an elevated view of another high-pressure container 500 and another temperature-control holder 600 in accordance with present disclosure.
Figure 7:
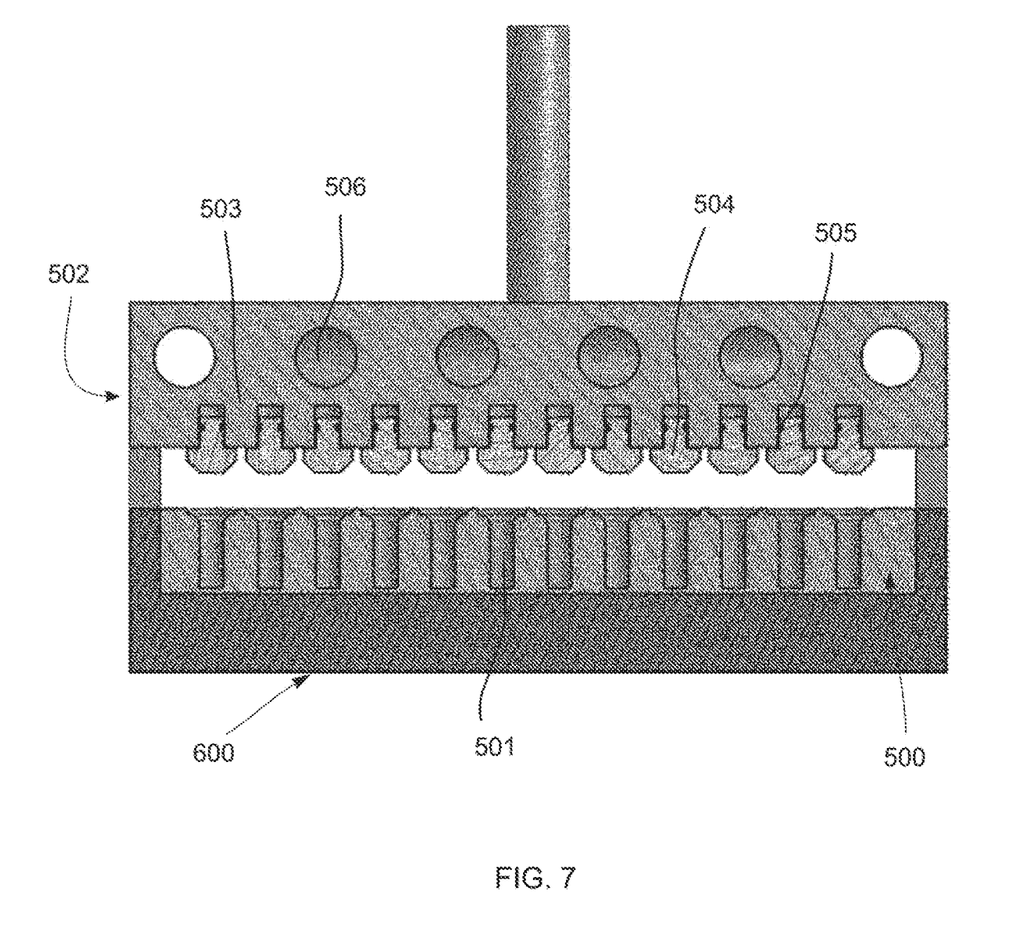
FIG. 7 is a cross-sectional view of high-pressure container 500 of FIG. 6 and another nucleating-lock 502 in accordance with present disclosure.

In another embodiment displayed in FIG. 6 and FIG. 7, the high-pressure container 500 has multiple small-volume cavities 501, for example 96 cavities, for holding the testing biomaterial solution. This high-pressure container 500 can be placed inside a temperature-control holder 600. The cavities 501 are closed with a nucleating-lock 502 with multiple plugs 504 with retainers 505. In this embodiment the nucleating-lock 502 has plugs 504 attached to a common compressing-lid 503 by using a retainer 505 to prevent its detachment from the compressing-lid. In this alternative, the common compressing-lid 503 has sufficient size to have temperature control means, for example by internal circulation of a coolant 506. Therefore, in this embodiment the nucleation-lock holder for cooling the plugs is not necessary.

The high-pressure container 500 with multiple small-volume cavities 501 can be used according to the method previously described. Briefly, the holder 600 with the high-pressure container acts as the temperature-control holder 300. When the plugs reach the desired nucleating temperatures, all the wells are closed at same time by imposing pressure in the compressing-lid, using a force driver. This generates the double action of closing the containers while nucleating water crystals of the biomaterial solution and ensuring the consistency of the temperature-time profile in all the multiple samples.

Figure 8:
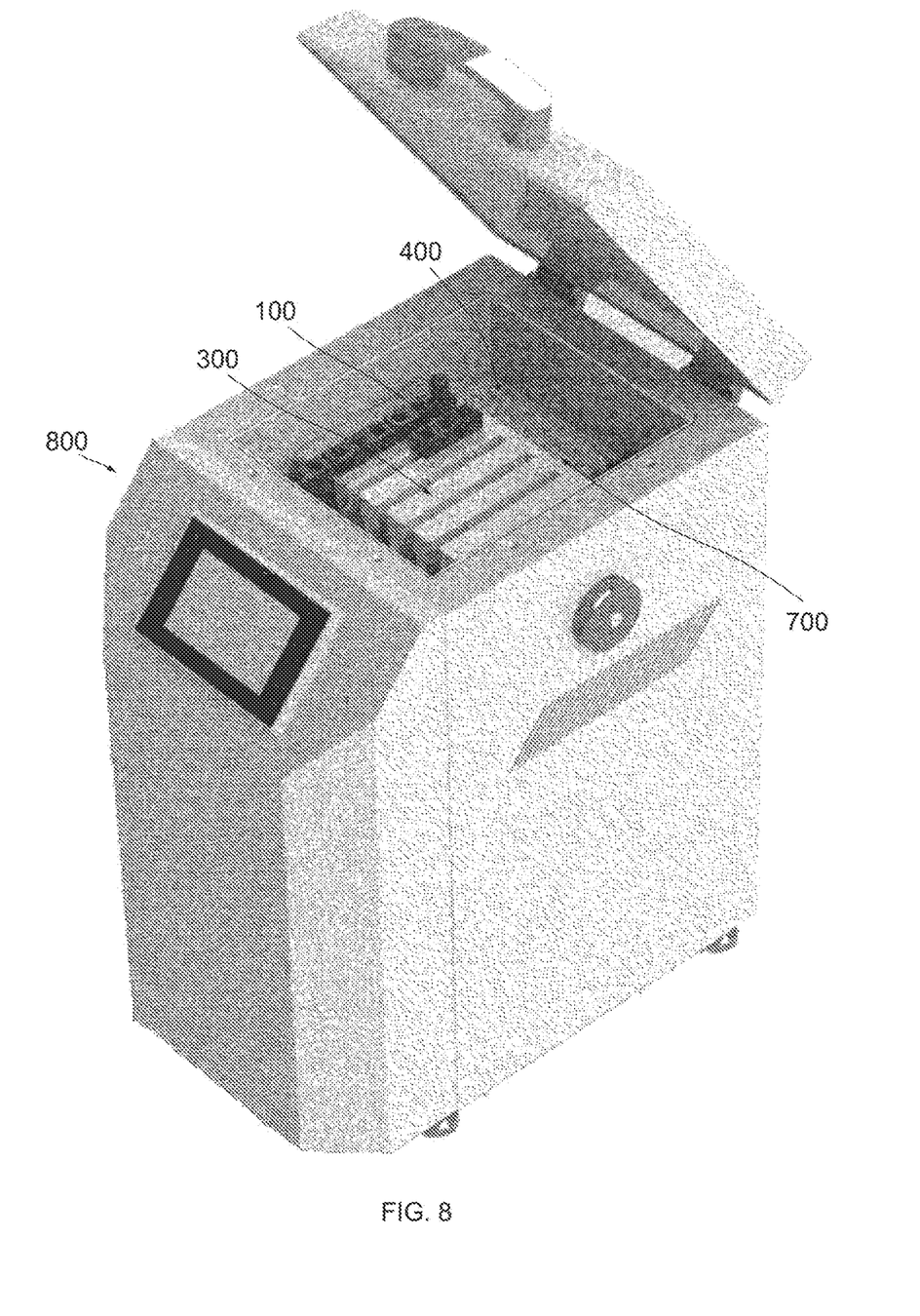
FIG. 8 is an elevated view of an apparatuses 800 for measuring degradation kinetics of biomaterials in aqueous solutions below the normal freezing temperature comprising an insulated low-temperature gradient chamber 700, with a temperature-control holder 300 for high-pressure containers 100 and nucleating-locks 400 in accordance with present disclosure.

The method described above can be implemented by using an apparatus 800 for measuring degradation kinetics of biomaterials in aqueous solutions below the normal freezing temperature comprising an insulated low-temperature gradient chamber 700, with a temperature-control holder 300 for high-pressure containers 100 and nucleating-locks. A holder 400 to cool the nucleating-locks to the nucleation temperature is also desirable for consistency and ease of operation. Said apparatus may further comprise a heat-exchange mechanism and control utility for controlling the operational steps of the method. The control utility may also comprise a computer and a user interface allowing a user to control the operational steps of the method.

REFERENCES

Brummitt, R. K. et al., 2011. Nonnative Aggregation of an IgG1 Antibody in Acidic Conditions, Part 2: Nucleation and Growth Kinetics with Competing Growth Mechanisms. *Journal of Pharmaceutical Sciences*, 100(6), pp. 2104-2119.

Rosa, M. et al., 2013. Measuring and modeling hemoglobin aggregation below the freezing temperature. *Journal of Physical Chemistry B*, 117(30), pp. 8939-8946.

Rosa, M., Roberts, C. J. & Rodrigues, M. A., 2017. Connecting high-temperature and low-temperature protein stability and aggregation J. M. Sanchez-Ruiz, ed. *PLOS ONE*, 12(5), p.e0176748.

The invention claimed is:

1. A method for preparation of a sample for measuring degradation kinetics of a biomaterial in aqueous solution, comprising the steps of:
    filling a high-pressure container with the biomaterial in aqueous solution and submitting said biomaterial to a temperature below the freezing temperature of the biomaterial at atmospheric pressure;
    closing the high-pressure container with a nucleating-lock, wherein the nucleating-lock comprises a compressing-lid and a plug with a retainer, wherein the retainer prevents detachment of the plug from the high-pressure container, and wherein the retainer insulates the plug from the compressing-lid at a temperature below the freezing temperature of the biomaterial at atmospheric pressure;
    allowing the high-pressure container to reach a pre-determined temperature different from the freezing temperature of the biomaterial at atmospheric pressure;
    wherein the tip of the plug of the nucleating-lock contacts the surface of the biomaterial solution inducing the nucleation whereby an ice layer is formed acting as a natural piston and ensuring isochoric conditions;
    removing the high-pressure container at a selected time and placing it at a temperature higher than the freezing temperature of the biomaterial at atmospheric pressure; and
    opening the high-pressure container and recovering the biomaterial in aqueous solution.

2. The method according to claim 1, wherein the step of filling the high-pressure container with the biomaterial in aqueous solution and submitting said biomaterial to the temperature below the freezing temperature of the biomaterial at atmospheric pressure is carried out at a temperature of 0.1° C. to 3° C. below the freezing temperature of the biomaterial.

3. The method according to claim 1, wherein the step of closing the high-pressure container with the nucleating-lock is performed with said nucleating-lock being at least 10° C. below the freezing temperature of the biomaterial at atmospheric pressure.

4. The method according to claim 1, wherein the step of allowing the high-pressure container to reach the pre-determined temperature is carried out by allowing the high-pressure container to reach −30° C. to 0° C.

5. The method according to claim 1, wherein the selected time is at least 5 min.

6. The method according to claim 1, wherein the biomaterial in aqueous solution is selected from a protein, an amino acid, a peptide, DNA, RNA, or mixtures thereof.

7. An apparatus for preparing a sample of a biomaterial for measurement of degradation kinetics in an aqueous solution below a freezing temperature of the biomaterial at atmospheric pressure, comprising:
    a high-pressure container;
    an insulated low-temperature gradient chamber comprising a temperature-control holder for the high-pressure container, and
    a nucleating-lock for inducing the nucleation of water crystals while closing the high-pressure container,
    wherein the temperature of the high-pressure container is controlled by a temperature-control holder;
    the temperature-control holder further comprising a holder for cooling the nucleating-locks to a nucleation temperature;
    wherein the nucleating-lock comprises a compressing-lid and a plug with a retainer;
    wherein the plug of the nucleating-lock comprises a cavity;
    wherein the cavity further comprises a nucleating agent.

8. The apparatus according to claim 7, wherein the temperature-control holder comprises eccentric wheel, levers, screws or hydraulic pistons for positioning the temperature-control holder at different heights in the insulated low-temperature gradient chamber.

9. The apparatus according to claim 7, wherein the temperature-control holder comprises a heater.

10. The apparatus according to claim 7, wherein the high-pressure container has multiple cavities.

11. The apparatus according to claim 7, wherein the high-pressure container has multiple cavities and wherein each cavity has two opposing openings.

12. The apparatus according to claim 7, wherein the nucleating-lock comprises multiple plugs with retainers.

13. The apparatus according to claim 7, wherein the plug of the nucleating-lock comprises a nucleating agent coated by a water permeable material.

14. The apparatus according to claim 7, wherein the insulated low-temperature gradient chamber further comprises a heat exchange mechanism on a bottom surface thereof.

15. An apparatus for preparing a sample of a biomaterial for measurement of degradation kinetics in an aqueous solution below a freezing temperature of the biomaterial at atmospheric pressure, comprising:
- a high-pressure container;
- an insulated low-temperature gradient chamber comprising a temperature-control holder for the high-pressure container, and
- a nucleating-lock for inducing the nucleation of water crystals while closing the high-pressure container,
- wherein the nucleating-lock comprises a compressing-lid and a plug with a retainer, wherein the retainer prevents detachment of the plug from the plug and compressing-lid assembly, and wherein the retainer insulates the plug from the compressing-lid,
- wherein the temperature-control holder comprises a heater.

* * * * *